United States Patent [19]

Nishiyama et al.

[11] 4,392,916

[45] Jul. 12, 1983

[54] PAPER-MAKING PROCESS WITH REGENERATED CHITIN FIBERS

[75] Inventors: Masashi Nishiyama, Kanonji; Yoshinari Kobayashi, Kagawa; Seiichi Tokura; Norio Nishi, both of Sapporo, all of Japan

[73] Assignees: Director-General of the Agency of Industrial Science and Technology, Tokyo; President of Hokkaido University, Hokkaido, both of Japan

[21] Appl. No.: 351,636

[22] Filed: Feb. 23, 1982

Related U.S. Application Data

[63] Continuation-in-part of Ser. No. 235,588, Feb. 18, 1981, abandoned.

[30] Foreign Application Priority Data

Jun. 17, 1980 [JP] Japan .................................. 55-82258

[51] Int. Cl.$^3$ ............................................. D21H 5/12
[52] U.S. Cl. .................. 162/157.1; 162/158; 162/146
[58] Field of Search ........................ 162/157 R, 158; 264/186; 536/20

[56] References Cited

U.S. PATENT DOCUMENTS 3,988,411 10/1976 Capozza ............................. 264/186
4,029,727 6/1977 Austin et al. ......................... 536/20
4,059,457 11/1977 Austin ................................. 536/20

FOREIGN PATENT DOCUMENTS 13181 7/1980 European Pat. Off. .............. 536/20
49-21241 5/1974 Japan ................................ 162/157 C

OTHER PUBLICATIONS

Battista O. A. "Synthetic Fibers in Papermaking" 1976 pp. 289-291.

Primary Examiner—William F. Smith
Attorney, Agent, or Firm—Brisebois & Kruger

[57] ABSTRACT

The invention provides a novel method for making paper of regenerated chitinous fibers without the use of any binder materials. By virtue of the inherent physiological inertness of the chitinous fibers and the absence of any binder materials, the paper obtained by the inventive method is advantageously used in medical treatment in contact with living body tissues. The principle of the method is that the chitinous fibers prepared by a wet spinning process are never brought into a dry condition or always kept wet with water down to the step of sheet making so that the self-bonding power of the fibers by the hydrogen bonding is never decreased and a chitinous paper with sufficient strengths can be prepared without a binder material. Alternatively, once dried chitinous fibers can be treated with a hydrogen-bond forming agent, e.g. urea, so that the sheet making is equally successful without the use of a binder material.

4 Claims, No Drawings

PAPER-MAKING PROCESS WITH REGENERATED CHITIN FIBERS

BACKGROUND OF THE INVENTION

This is a continuation-in-part application of the U.S. patent application Ser. No. 235,588 filed Feb. 18, 1981 now abandoned.

The present invention relates to a method for making a paper which is relatively free from rejection by a living body tissue of human or, more particularly, to a method for making a paper made at least partially of fibers of a regenerated chitinous material.

Needless to say, ordinary papers are made of cellulosic fibers derived from wood or other natural origins. In addition to these traditional papers made of natural cellulosic fibers, there have been recently developed various kinds of papers made of a man-made fibrous material such as regenerated cellulose, e.g. rayon, as well as various synthetic fibers.

On the other hand, it is a recent trend in the medical technology that papers are more and more widely used in the therapeutical treatment as a material to be applied to human body tissues. As the fibrous materials of which conventional papers are made have so widely different chemical and physiological properties from the living body tissues, there have been problems in the application of paper materials to a human body that the paper material causes inflammation on the skin or is rejected by the living tissue. Accordingly, it has been eagerly desired to develop a paper which is relatively free from the above problems with high affinity to a living body tissue.

In order that a paper may have a high affinity to living tissues, the fibers per se of which the paper is composed should also have high affinity to living tissues. It is a due consequence that fibers of animal origin would have a higher affinity to living tissues than those of vegitable origin such as cellulosic fibers and synthetic polymers. Among such fibers of animal origin, one of the most promising ones is the fibers of chitin.

As is well known, chitin is a polymeric substance widely occurring in nature as one of the main components of the crusts of many arthropods such as crustaceans, e.g. lobsters and crabs, insects, e.g. locusts and beetles, as well as in certain fungi including mushrooms and molds. Chitin is a kind of polysaccharides composed of the polycondensate of N-acetyl-D-glucosamine with $\beta$-1,4-glucoside linkages.

It is known that fibers of chitin can be prepared by wet or dry spinning of a solution of chitin and application of chitin fibers to adsorbent paper or swabs is suggested (see, for example, U.S. Pat. No. 3,988,411). A problem in the paper making process of chitin papers is the relatively weak self-bonding strength of chitin fibers so that paper of chitin fibers having sufficient mechanical strengths can hardly be obtained unless a considerably large amount of a binder material is used.

It may be too much to say that such a binder material contained in the paper of chitin fibers causes another trouble when the paper is used in a medical treatment in contact with the living tissues. Therefore, it has been eagerly desired to develop a method for making paper of chitin fibers having sufficiently high mechanical strengths without the use of any binder material and various attempts have been made without noticeable success.

SUMMARY OF THE INVENTION

It is therefore an object of the present invention to provide a novel method for making paper of chitin fibers having sufficiently high mechanical strengths without the use of any binder material so as not to cause any troubles when the paper is used in contact with living body tissues.

The extensive investigations undertaken by the inventors to solve the above problem led to a conclusion that hydrogen bonds between the regenerated chitin fibers play the most important role in the self-bonding of chitin fibers when no binder material is used in paper making and that the power of hydrogen bonding is lost to a great extent once the chitin fibers are dried.

Accordingly, the process of the invention for making a paper of chitin fibers comprises the steps of (a) preparing a dope by dissolving chitin, alkylated chitin or acetylated chitin in a solvent, (b) spinning the dope through a spinning nozzle into a coagulating bath to form fibers, preferably, having a fineness of 10 denier or smaller, if necessary, with drawing, (c) chopping the fibers into staples each having a length, preferably, not exceeding 30 mm, (d) dispersing the staples into a pulp suspension, and (e) subjecting the pulp suspension to sheet making, in which the fibers formed in the step (b) are subsequently kept wet with water throughout down to the step (e).

Alternatively, the regenerated chitin fibers once dried can be subjected to paper making to give a paper having sufficiently high mechanical strengths when the fibers are treated with a hydrogen bond forming agent such as urea before they are subjected to paper making.

DETAILED DESCRIPTION OF THE PREFERRED EMBODIMENTS

As is mentioned before, chitin is mostly obtained from a natural animal source and is a kind of polysaccharides composed of the polycondensate of N-acetyl-D-glucosamine with $\beta$-1,4-glucoside linkages.

Notwithstanding the seeming resemblance of the chemical structure to that of cellulose, chitin has physical and chemical properties and exhibits behaviors quite different from those of cellulose and, moreover, it is characteristically inert to or rather affinitive to living body tissues. Processes for the preparation of an alkylated chitin or acetylated chitin are well known in the art.

Similarly to cellulose, most of the conventional organic solvents have no dissloving power for chitin and its derivatives and a solution of chitin or its derivative can be prepared only by the use of a specific solvent. It is known that films or fibers can be shaped with a solution of chitin or its derivatives (see, for example, Japanese Patent Disclosure No. 53-126090) but such shaped materials have limited applications due to the disadvantage in the costs and certain technical drawbacks in comparison with conventional cellulose-based papers.

The inventors have made attempts to obtain papers having good affinity to living body tissues and arrived at an idea that chitin or its derivatives may be a promising material as being mostly of animal origin of abundant supply and fibers of chitin or its derivative would be able to be shaped into papers forming fiber-to-fiber bonding not only through the hydrogen bonds but also through the ionic linkages by virtue of the cationic groups bonded to the skeletal structure of the molecule reaching the establishment of the present invention after extensive investigations.

Different from naturally occurring cellulose fibers, regenerated cellulose fibers obtained by the viscose process or cuprammonium process with natural cellulose as the starting material have markedly decreased molecular orientation in the course of regeneration from a dope and fiber-to-fiber bonding through the hydrogen bonds between the fiber molecules are hardly formed resulting in insufficient paper formation. Therefore, such a kind of regenerated cellulosic fibers can be processed into papers such as the so-called rayon paper only by the aid of a suitable binder material, e.g. a water-soluble polymeric substance such as a polyvinyl alcohol and a polymer emulsion such as an acrylic resin emulsion unless certain measures are undertaken upon the fibers, for example, to increase the specific surface area of the fibrous material.

On the contrary, chitin has a molecular structure in which aminoacetyl groups are substituted for the hydroxy groups of cellulose at the $C_2$ position so that the regenerated fibers obtained from chitin are readily gelled and firm fiber-to-fiber bonding is readily formed even without the addition of a binder material owing partly to the electrostatic interaction between the anionic hydroxy groups and the cationic aminoacetyl groups.

The above mentioned characteristic of interfiber self-bonding is particularly advantageous when the paper made of the regenerated chitin fibers is intended to be used in medical treatment because the paper can be absolutely free from any additive ingredients which may cause some problems against living body tissues in addition to the physiological inertness inherent to the chitin fibers. Thus, the regenerated fibers of chitin or its derivatives can be made into papers in a conventional paper making process with a paper stock containing the fibers alone as dispersed therein without any binder material to give papers most advantageously used in medical purposes with high safety only if the chitin fibers regenerated from a dope are never brought under a dry condition down to the step of paper making. Needless to say, fibers of other kinds such as cellulosic and synthetic fibers may be added in the paper stock preparation safely, if desired, in combination with the chitinous fibers.

The starting material of the inventive paper includes not only chitin per se but also derivatives thereof such as alkylated chitins and acetylated chitins. Examples of the alkylated chitins are O-methylchitin, O-ethylchitin, O-n-propylchitin, O-isopropylchitin, O-n-butylchitin, O-isobutylchitin, O-sec-butylchitin, O-tert-butylchitin, O-n-amylchitin, O-isoamylchitin, O-tert-amylchitin and the like. Examples of the acetylated chitins are monoacetylchitin and diacetylchitin. Generally speaking, it is a trend that fibers of a chitin derivative having more bulky substituent groups are more highly susceptible to gelation and have a higher strength of interfiber self-bonding presumably due to the partially disordered orientation of the molecules.

The spinning dope used in the inventive method is prepared by dispersing the chitin or its derivative in an organic acid such as dichloroacetic acid or a mixture of the same with an inert organic solvent such as a halogenated hydrocarbon and alternately repeating freezing and thawing the mixture to give a homogeneous solution. The concentration of the chitin in the dope is preferably in the range from 0.5 to 20% by weight depending on the solubility thereof in the solvent used. Suitable viscosity of the dope is in the range from 100 to 5000 poise or, preferably, from 500 to 2000 poise at the spinning temperature.

The thus prepared dope of the chitin or its derivative is extruded through a spinning nozzle into a coagulating bath to be shaped into fibers. The coagulating bath is not particularly limitative and a solvent or a solvent mixture of any kind which is a precipitant for chitin or its derivative may be used. Particularly preferred solvents for the coagulating bath are esters such as ethyl acetate, propyl acetate and the like, ketones such as acetone and the like and alcohols such as methyl alcohol, ethyl alcohol and the like as well as water in some cases. These solvents may be used either singly or as a mixture of two kinds or more according to particular needs. It is sometimes advantageous that two or more of the coagulating baths are prepared, if necessary, each with a different solvent from the other and coagulation is carried out by successively passing the fibers as extruded from the nozzle through these baths so that the coagulation rate of the fiber from the skin layer to the core may be controlled more adequately.

The fibers obtained by the coagulation are drawn or stretched in a suitable stretching ratio of, say, up to 300% to improve the tensile properties of the fibers as well as to adjust the fineness of the fibers. Stretching of the fibers must, of course, be carried out in wet or, preferably, in water. The fibers should have a fineness not exceeding 10 denier because certain difficulties are encountered in paper making with coarser fibers without a binder material due to the decrease in the relative interfiber self-bonding strength and increase in the stiffness.

The fibers are freed from the solvents as the coagulating bath by washing with water either before or after stretching above mentioned. The thus washed and stretched fibers are then chopped into staples having a length suitable for sheet making. If necessary, the fibers are washed prior to water wash with a water-miscible organic solvent such as ethyl alcohol to remove any trace amount of the organic acid used for the preparation of the spinning dope. It is also necessary to carry out chopping with wet fibers. The length of the staples naturally depends on the process of sheet making performed with a variety of paper making machines. It should usually not exceed 30 mm for each of the staple fibers since longer staples have poor dispersibility in water and uniformity of the paper weight cannot be expected resulting in inferior behavior in the paper formation.

The chopped staples of the chitin fibers are then, without being dried, dispersed in water to give a fiber suspension. If necessary to increase the dispersibility of the staples in water, though not desirable, certain mucilaginous materials may be added to the suspension such as the naturally occurring mucilages obtained from, for example, the root of Hibiscus manihot L. and the wood of Hydrangea paniculata var. floribunda or synthetic water-soluble dispersants such as plyacrylamide and polyethyleneoxide. The concentration of the staples of the chitin fibers in the fiber suspension is determined in accordance with the desired basis weight of the paper and the process for the sheet making utilized as well as the length of the staples. Usually it is below 3% or, preferably, in the range from 0.1 to 1.0%. Other kinds of paper-forming fibrous materials such as wood pulp, synthetic pulp, rayon fibers and the like may be admixed into the fiber suspension if allowed by the intended use of the paper.

The sheet making process with the above prepared paper stock is rather conventional and various types of conventional paper making machines can be used. Paper making by handwork is of course suitable.

In the above described paper making process with the chitin fibers, the fibers obtained by regenerating from the dope are kept wet throughout down to the step of sheet making never being in a dry condition and the thus obtained chitinous paper has unexpectedly high mechanical strengths despite the absence of any binder material, presumably, by virtue of the strong interfiber self-bonding as a result of the hydrogen bonding between the fibers which may be lost once the fibers are dried.

In view of the burdensomeness in keeping the regenerated chitin fibers in a wet condition throughout, the inventors have further conducted to discover a method for obtaining chitinous papers with once dried chitin fibers arriving at a discovery that the use of certain kinds of hydrogen-bond forming agents is effective in increasing the mechnical strengths of the chitinous paper prepared using once dried chitin fibers. Several examples of the above mentioned hydrogen-bond forming agents are dipolar aprotic compounds such as urea, dimethylformamide, N-methylpyrrolidone and the like, dichloroacetic acid and mineral acids, of which urea is the most preferred from the standpoint of inexpensiveness. When urea is used as the hydrogen-bond forming agent, the dried chitin fibers are dipped in an aqueous solution of urea in a relatively high concentration such as, for example, 80% by weight or higher for at least several hours followed by thorough washing with water and dispersing in water to give a fiber suspension for sheet making. It is of course that the chitin fibers taken out of the urea solution must never be brought into a dry condition before dispersing them in water. Dichloroacetic acid is used preferably as diluted with dichloroethane in a concentration of, for example, about 20% by weight and sulfuric acid as an example of the mineral acids is used in a concentration of about 20% by weight. The mechanical strengths of the chitinous paper obtained in the above described process including the treatment of the dry fibers with a hydrogen-bond forming agent are almost identical with those of the papers prepared in the wetthrough process.

The papers prepared in the above described manner with the fibers of regenerated chitin or its derivative are porous and have good air permeability as well as good water absorptivity owing to the absence of any binder materials in addition to the high mechanical strengths so that they are very useful in the medical treatment of living bodies.

Following are the examples to illustrate the inventive paper making process in further detail.

EXAMPLE 1

A mixture composed of 7.7 parts by weight of chitin and 91.4 parts of weight of formic acid was repeatedly frozen and thawed so that the chitin was gelled in the formic acid and then 7.7 parts by weight of dichloroacetic acid were added to the mixture whereupon the gelled chitin was dissolved in the mixed solvent of formic acid and dichloroacetic acid to give a uniform dope from which suspended fine particles were removed by use of a membrane filter.

The dope was extruded through a spinning nozzle of platinum having 50 holes of each 0.1 mm diameter into a first coagulating bath of ethyl acetate and then into a second coagulating bath of methyl alcohol into filaments followed by introducing the filaments into a water bath in which the filaments were drawn in a stretching ratio of 1.34 times. The thus stretched filaments were wound around a reel without being dried.

The thus obtained regenerated chitin fibers had a fineness of 3.0 denier and a single fiber strength of 1.0 g/denier. They were translucent and had a pleasant appearance and touch.

The fibers were thoroughly rinsed in running water and chopped in wet into staples of each having a length of about 5 mm. The chopped staples were uniformly dispersed in water and the suspension was subjected to sheet making according to the procedure specified in JIS P No. 8209 into a thin leafy paper similar to handmade Japenese paper in appearance. It had a basis weight of 65 g/m$^2$, density of 0.43 g/cm$^3$, breaking length of 1.13 km and burst factor of 1.11.

EXAMPLE 2

Fibers of a n-butylchitin were prepared in the same manner as in Example 1 with a stretching ratio of 1.41 times. The fibers were thoroughly rinsed in ethyl alcohol to be freed of any trace amount of the organic acid used in the spinning dope before washing with water. The fibers had a fineness of about 1.0 denier. The staples each having a length of about 5 mm obtained by chopping the regenerated n-butylchitin fibers were uniformly dispersed in water and made into a uniform, thin leafy paper in the same manner as in Example 1. The paper had a basis weight of 116.8 g/m$^2$, density of 0.81 g/cm$^3$, breaking length of 3.42 km and burst factor of 3.42.

EXAMPLE 3

Fibers of a n-amylchitin were prepared in the same manner as in Example 2 with a stretching ratio of 1.38 times. The fibers had a fineness of about 1.0 denier. The staples each having a length of about 7 mm obtained by chopping the above regenerated n-amylchitin fibers were uniformly dispersed in water and made into a uniform, thin leafy paper in the same manner as in Example 1. The paper had a basis weight of 93.3 g/m$^2$, density of 0.72 g/cm$^3$, breaking length of 3.86 km, burst factor of 2.46 and folding endurance of 67 times at 0.5 kg load.

COMPARATIVE EXAMPLE

The regenerated chitin fibers obtained in Example 1 were thoroughly rinsed with water and, after complete drying at 80° C., chopped into staples of 5 mm length, which were then dispersed in water to make a fiber suspension without using a binder material and subjected to the sheet making test according to the procedure specified in the JIS. The results were that the wet sheet of the chitin fibers could not be peeled off the filter paper as the backing support to retain the form of a sheet so that no chitin paper could be obtained.

EXAMPLE 4

The dried staples of the chitin fibers prepared in Comparative Example above were dipped in an aqueous solution containing 80% by weight of urea at room temperature and kept standing for 24 hours and, after thorough rinse with water, a fiber suspension was prepared using no binder material with the staples kept in water without causing drying. The sheet making test undertaken in the same manner as in Example 1 could be performed without particular difficulties and the resultant paper of the regenerated chitin had a breaking length of 0.8 km and a burst factor of 0.7.

EXAMPLE 5

The dried staples of the chitin fibers prepared in Comparative Example above were dipped in dichloroethane containing 20% by weight of dichloroacetic acid at room temperature for 2 hours followed by thorough rinse with water and, without being brought into a dry state thereafter, dispersed in water into a fiber suspension which was subjected to sheet making in the same manner as in Example 1. No particular difficulties were encountered in this sheet making test and the paper of the regenerated chitin fibers thus obtained had a breaking length of about 1.1 km.

What is claimed is:

1. A method for the preparation of a paper composed of chitinous fibers without the use of a binder material which comprises the steps of
   (a) preparing a dope by dissolving chitin, an alkylated chitin or an acetylated chitin in a solvent,
   (b) spinning the dope through a spinning nozzle into a coagulating bath to form fibers,
   (c) chopping the fibers into staples,
   (d) dispersing the staples of the fibers in water to make a fiber suspension, and
   (e) subjecting the fiber suspension to sheet making, in which the fibers formed in the step (b) are subsequently kept wet with water throughout down to the step (e).

2. A method for the preparation of a paper from once dried fibers of a regenerated chitinous material of chitin, an alkylated chitin or an acetylated chitin by subjecting a fiber suspension of the chitinous fiber to sheet making without the use of a binder material which comprises contacting the once dried chitinous fibers with a hydrogen-bond forming agent and rinsing the thus treated chitinous fibers with water subsequently keeping the fibers wet with water down to the step of the sheet making.

3. The method as claimed in claim 2 wherein the hydrogen-bond forming agent is selected from the group consisting of an aqueous solution of a dipolar aprotic compound, dichloroacetic acid and a mineral acid.

4. The method as claimed in claim 3 wherein the dipolar aprotic compound is urea.

* * * * *